United States Patent
Batey

(10) Patent No.: US 9,081,206 B2
(45) Date of Patent: Jul. 14, 2015

(54) EYEWEAR

(71) Applicant: Lee Peter Batey, Darwin (AU)

(72) Inventor: Lee Peter Batey, Darwin (AU)

(*) Notice: Subject to any disclaimer, the term of this patent is extended or adjusted under 35 U.S.C. 154(b) by 0 days.

(21) Appl. No.: 13/923,493

(22) Filed: Jun. 21, 2013

(65) Prior Publication Data

US 2013/0293826 A1 Nov. 7, 2013

Related U.S. Application Data

(63) Continuation-in-part of application No. 13/101,284, filed on May 5, 2011, now abandoned, which is a continuation-in-part of application No. PCT/AU2009/001469, filed on Nov. 5, 2009.

(30) Foreign Application Priority Data

Nov. 5, 2008 (AU) .............................. 2008905706
Jun. 18, 2013 (AU) .............................. 2013206397

(51) Int. Cl.
| | | |
|---|---|---|
| *G02C 11/08* | (2006.01) | |
| *G02C 5/00* | (2006.01) | |
| *A61F 9/02* | (2006.01) | |
| *A63B 33/00* | (2006.01) | |
| *G02C 3/00* | (2006.01) | |

(52) U.S. Cl.
CPC . *G02C 5/001* (2013.01); *A61F 9/02* (2013.01); *A61F 9/026* (2013.01); *A63B 33/002* (2013.01); *G02C 3/003* (2013.01); *G02C 11/08* (2013.01)

(58) Field of Classification Search
CPC .......... G02C 3/003; G02C 5/16; G02C 11/08; G02C 2200/06; G02C 5/001; A61F 9/26; A61F 9/28; A61F 9/27
USPC ..................... 351/41, 62, 111–123, 158, 156; 2/435–437
See application file for complete search history.

(56) References Cited

U.S. PATENT DOCUMENTS

| | | | |
|---|---|---|---|
| 2,430,881 A | 11/1947 | Lehmberg | 2/437 |
| 4,288,891 A | 9/1981 | Boden | 24/115 |
| 5,197,166 A | 3/1993 | Meier et al. | 24/115 |
| 5,347,323 A * | 9/1994 | Wilson | 351/44 |
| 5,666,699 A | 9/1997 | Takahashi | 24/115 |
| 5,671,505 A | 9/1997 | Anscher | 24/115 |
| 5,778,904 A | 7/1998 | Elsner | 132/275 |
| 6,247,811 B1 * | 6/2001 | Rhoades et al. | 351/156 |
| 8,235,523 B2 * | 8/2012 | Yang | 351/43 |
| 8,517,533 B2 * | 8/2013 | Razin | 351/156 |
| 2005/0259219 A1* | 11/2005 | Helbrecht | 351/116 |
| 2009/0188023 A1* | 7/2009 | Hsu | 2/436 |

OTHER PUBLICATIONS

U.S. Appl. No. 13/101,284, filed May 5, 2011, Lee Peter Batey.

* cited by examiner

*Primary Examiner* — Huy K Mai
(74) *Attorney, Agent, or Firm* — Stein IP LLC

(57) ABSTRACT

Eyewear for use by a wearer, said eyewear providing a substantially fluid tight seal about the wearer's eyes, the eyewear including at least one lens for positioning at least partially in front of a wearer's eyes; a frame adapted to mount the at least one lens for positioning the at least one lens in front of the eyes of the wearer; head mounting means adapted to attach the frame relative to a wearer's head; and at least one seal attached relative to said frame and located about a periphery of the wearer's eyes wherein the eyewear is wearable in a substantially fluid tight condition in which the at least one seal forms a substantially fluid tight seal about the wearer's eyes, and a free condition in which the eyewear is wearable with the seal spaced from the wearer's eyes.

19 Claims, 15 Drawing Sheets

EYEWEAR

FIELD OF THE INVENTION

The present invention relates to eyewear and particularly to eyewear adapted to be used as glasses and also provide an air/water tight seal between the glasses and the wearer's face.

BACKGROUND ART

There are many endeavours in which the participant is preferably equipped with the eyewear that protects the wearer's eyes from hostile or annoying elements of the environment.

Examples of hostile elements include water, chemicals (whether waterborne or airborne), extreme temperature, or airborne particulars such as dust, dirt, smoke and the like, and sunlight.

Traditional eyeglass solutions provide a wearer with the basic protection from sunlight with some ancillary protection from more hostile conditions. Traditional goggle-type solutions manufacture a flexible seal material which is can be deformed to the shape of the wearer's face through the application of tension to the frame using a flexible strap. The flexible strap pulls the eyeglass frame against the wearer's face to provide an air/watertight seal between the eyeglass frame and the wearer's skin.

Various materials have been used to form the seal but most cause skin irritation and do not adequately shape to the individual's facial contours. Further, providing a more rigid seal material can result in constricting blood circulation to areas surrounding the eye socket when tension is applied. Consequently, the eyewear of this form cannot be used for extended periods of time.

Still further, goggle-type solutions do not generally provide vision correction and must either be worn in conjunction with the wearer's eyeglasses or, custom-made goggles must be used which are generally expensive and cannot be mass produced. Carrying multiple types of eyewear is extremely inconvenient.

It will be clearly understood that, if a prior art publication is referred to herein, this reference does not constitute an admission that the publication forms part of the common general knowledge in the art in Australia or in any other country.

SUMMARY OF THE INVENTION

The present invention is directed to eyewear, which may at least partially overcome at least one of the abovementioned disadvantages or provide the consumer with a useful or commercial choice.

With the foregoing in view, the present invention in one form, resides broadly in eyewear for use by a wearer, said eyewear adapted to provide a substantially fluid tight seal about the wearer's eyes, the eyewear including at least one lens for positioning at least partially in front of a wearer's eyes, a frame adapted to mount the at least one lens for positioning the at least one lens in front of the eyes of the wearer; head mounting means adapted to attach the frame relative to a wearer's head, and at least one seal attached relative to said frame and located about a periphery of the wearer's eyes wherein the eyewear is wearable in a substantially fluid tight condition in which the at least one seal forms a substantially fluid tight seal about the wearer's eyes, and a free condition in which the eyewear is wearable with the seal spaced from the wearer's eyes.

The present invention relates to eyewear having multiple functions, including being usable as traditional eyeglasses, as air/water tight goggles and as glasses that enable airflow around the lenses, with the lenses thereof also being capable of providing vision correction and/or sun protection for the wearer.

The eyewear of the present invention includes at least one lens. Normally, a pair of lenses may be provided. Alternatively, a single unitary or monolithic lens may be provided which extends substantially across the wearer's face. The at least one lens will be appropriately mounted on, or to, the frame. This mounting may result in the at least one lens being mounted "to" the frame which normally occurs with the unitary lens or "in" the frame (within eyewires or rims) as normally occurs when a pair of lenses are provided.

The lenses can be any type of lens known in the field. In particular, the lenses may be polarised, tinted, photochromic, UV resistant and/or UV protective, prescription, or provide impact protection.

It is also particularly preferred that the at least one lens provided according to the invention will be hydrophobic. This may be a particularly important feature as the eyewear of the invention is adapted for use in water and other hostile environments and should be capable of shedding liquid quickly to leave vision unobscured.

The lens may be attached to the frame of the eyewear in any suitable manner. For example, an opening in the frame adapted to receive a lens may be provided with a circumferential groove or similar in order to receive an edge of the lens or receive each lens therein. In an alternative and preferred form, the lens may be attached to the frame with a sealing member located between the lens and the frame.

The frame of the eyewear of the present invention is typically at least partially rigid. Frames for glasses and the like normally include at least some of the following components:
Frame front: Front part of the eyeglass frame that holds the lenses in place and bridges the top of the nose.
Eye wires (rims): Part of the frame front into which the lenses are inserted.
Bridge: The area between the lenses that goes over the nose and supports the majority of the weight of the eyeglasses. Examples include:
  A keyhole bridge is shaped like an old-fashioned keyhole and rests on the sides of the upper part of the nose. This style is for those with small or flat nose bridges.
  A saddle bridge is shaped like a saddle and spreads the weight of the frame across the sides and the top of the nose. This style works well for heavy glasses or for those who are sensitive to pressure. A preferred form of the present invention includes a deployable nose bridge/pad portion that is preferably moveable between a retracted position in which the bridge/pads function as an adjustable saddle bridge, and a deployed position in which the bridge/pads applies sufficient force to the sides of a user's nose to seal from water or other detritus. Normally the bridge/pads will be suitably sealed to the remainder of the frame or eyeglasses to seal against a user's face. The deployable nose bridge/pad portion is moveable using any suitable mechanism, but articulated arms form one mechanism. Further, the deployable nose bridge/pad portion is moveable substantially vertically but other directions of movement may be permitted or preferred. The movement may be manually driven or may be biased movement with a temporary hold and release mechanism.
  An adjustable bridge includes nose pads that can be adjusted for fit and comfort.

A double bridge has a reinforcing bar over the top of the bridge.

End pieces: Extensions of the frame front to which the temples are attached.

Hinges: Part of the frame that connects the frame front to the temples and allows the temples to swing.

Temples/earstems: Parts of the frame that extend over and/or behind the ears to help hold the frame in place.

Skull temples are the most popular for plastic frames. They are bent down slightly over the ear and follow the contour of the skull.

Comfort-cable temples hook behind the ear with a flexible metal cable and are good for children's glasses and for sport safety glasses.

Riding bow temples are similar to comfort-cables, except they are rigid and made of plastic.

Spring-hinged temples include hidden springs in the hinges that help keep the frame from slipping. They are sometimes more expensive, but usually more resistant to breakage.

Library (or paddle) temples are straight, so they can be slipped on and off easily. They are often used in reading glasses.

Nose pads: Plastic pieces that may be attached directly to the frame or to pad arms. They help keep the frame in its proper position.

Pad arms: Attachments that hold the nose pads in place and allow adjustments to help conform to the patient's bridge.

Top bar: A reinforcing bar that crosses the top of the glasses on some metal frames, popular in aviator glasses.

Temple tips: Plastic coatings that often cover the ends of the temples behind and/or over the ears.

Rimless frames (or mountings): The temples and bridge attach by mountings directly to the lenses without the use of eyewires or rims.

The frame of the present invention will typically be at least partially rigid. Normally, at least the frame front will be semi-rigid but flexible, but the bridge, end-pieces and/or earstems may also be semi-rigid but flexible. It is preferred that the frame portions including the frame front, including the bridge and end-pieces and typically the earstems as well, be sufficiently strong but deformable upon application of a sufficient force. The frame and lens(es) should be flexible enough to conform readily to the profile of a user's face.

The materials used in the production of modern eyeglass frames are normally plastic, metal, or a combination of the two (composites). Manufacturers select materials that are cost effective, adjust easily, offer safety and workability, hold the lenses properly, and resist breakage, corrosion, and heat. Popular frame materials include.

Plastics

Cellulose acetate (zylonite): The most commonly used plastic in eyeglass frames, cellulose acetate is relatively inexpensive, easy to work with, and comes in a wide variety of colors, textures, and patterns. The material is easily adjusted but tends to get brittle with age.

Cellulose proprionate: This is a lightweight material that can be injection molded making it ideal for intricate designs. Care must be taken when heating and adjusting frames made of this material because it will shrink and ruin with overheating.

Kevlar: Developed by DuPont for use in bulletproof vests, this plastic can withstand high impact such as that experienced in sporting events. The material is limited because it will not shrink or stretch, and it comes in few colors.

Nylon: Many sports and safety glasses are made of nylon because it is virtually unbreakable and relatively lightweight. The material is, however, difficult to adjust and can be manufactured only in darker colors. It can also become brittle over time.

Optyl: This material is somewhat lighter in weight than cellulose acetate and is hypoallergenic, an advantage to skin-sensitive patients. Frames made of optyl are more difficult to adjust because the material can return to its original molded shape, and the frames may break easily if not heated properly.

Polycarbonate: Polycarbonate is 10 times more impact-resistant than conventional plastic or glass and is the material of choice for children's, sports, and safety glasses. Polycarbonate lenses are thinner and lighter than conventional plastic or glass lenses, and the material comes with built-in ultraviolet protection.

Metals

Aluminum: Although very lightweight, aluminum is difficult to solder or weld, limiting its adaptability to different designs.

Cobalt: Usually used as part of a metal alloy, cobalt appears in high-quality frames that can be made lightweight, durable, flexible, and thin. It can also be successfully coated with a variety of colors, but is very expensive and consequently limited in use.

Monel: Monel is one of the most popular materials used in metal frames because it can be hammered into many shapes without losing its strength. It can also be made in various colors.

Nickel silver: This is a common material used in hinges, end pieces, and heavy bridges, and for the inner core of temples. It is more brittle than several other metals, making it less suited to the slender frames so popular today.

Phosphor bronze: This flexible alloy is about 95 percent copper, making it a good choice for temples.

Stainless steel: Stainless steel is one of the most corrosion-resistant metals, but is difficult to work with in the manufacturing process.

Trilam: This product is lightweight, however it has a shape memory, which can make frame adjustments difficult.

Composites

Carbon fiber graphite (CFG): CFG is a material made of nylon and carbon that provides the endurance of metal frames but is thin and lightweight. Although the material is black in its natural state, it is now available in a wide range of colors.

Copolyamide (MXP7): This material is a blend of nylon manufactured for frame-injection molding. The material is strong, lightweight, and durable, and it retains its shape unless heated.

Flexon7: Flexon7 is a proprietary material made from a titanium-based alloy with a high "memory" factor that enables a twisted frame to return to its original shape. In addition to making frames extremely durable, the Flexon material holds adjustments longer and is lighter in weight than traditional metal frames.

Titanium Ti-227: Titanium Ti-227 is nearly 50 percent lighter than most metal frame materials. It is hypoallergenic, non-corrosive, and one-third stronger than steel, making it an extremely desirable material for manufacturing frames. It's also difficult and expensive to extract and refine this abundant material.

Plastics or composite materials are particularly preferred given the use of the eyewear of the present invention in water and other hostile environments as well as the deformability required. However, a metal frame may find use if the seals are of sufficient quality.

The eyewear includes a head mounting means adapted to attach the frame relative to a wearer's head. The head mounting means of the eyewear of the present invention will typically include the earstems which are typically attached to the frame front. As stated previously, the earstems may be rigid or flexible.

Given that the eyewear of the present invention is intended to form a substantially air or fluid tight seal with a wearer's face, a more preferred means of mounting the eyewear relative to a wearer's head is to provide an adjustment strap attached to the eyewear and which extends substantially about the wearer's head. The adjustment strap may be associated with quick release mechanisms to enable multiple users of the eyewear and adjustment of the eyewear while in place on the head of the wearer.

In particular, the adjustment strap may be used with or without the earstems attached to the frame front.

In particular, a quick release clip or similar may be provided in order for a wearer to rapidly adjust the eyewear from the substantially fluid tight mode into the free mode and vice versa. One such example of a quick release clip or similar is known colloquially as a "cord lock". Obviously, this type of clip would only be suitable for use with a flexible type head mounting means.

Various cord locks are known in the art, perhaps the most prevalent of which are the "barrel" or "plunger" locks shown in U.S. Pat. No. 4,288,891 to Boden; U.S. Pat. No. 5,197,166 to Meier et al.; U.S. Pat. No. 5,666,699 to Takahashi; U.S. Pat. No. 5,671,505 to Anscher; and U.S. Pat. No. 5,778,904 to Elsner.

One preferred cord lock has an aperture that allows a drawstring to be pulled through it when the lock is squeezed together. When not squeezed, a spring in the lock causes a movable portion within the barrel to press against the drawstring and prevent movement of the lock with respect to the drawstring.

Other means of mounting the eyewear relative to a wearer's head may be used, however it is important that the frame of the eyewear is retained relatively closely to the wearer's face at all times when the eyewear is being worn, and particularly when the eyewear is in the substantially air/fluid tight condition.

The eyewear includes at least one seal attached relative to said frame and located about a periphery of the wearer's eyes wherein the eyewear is wearable in a substantially fluid tight condition in which the at least one seal forms a substantially fluid tight seal about the wearer's eyes, and a free condition in which the eyewear is wearable with the seal spaced from the wearer's eyes.

The at least one seal therefore it is preferably provided as a peripheral seal around one or more the wearer's eyes. The at least one seal may be provided as a peripheral seal around the lens(es) of the eyewear.

The at least one seal of the present invention may be provided in either the free or the fluid tight conditions and once released, may be biased into the other of the conditions.

The at least one seal is movable between the free and sealed conditions. Preferably, this movement may be provided by moving either the seal relative to the frame, or, the seal may be provided in a fixed relation to the frame and the frame may be moved relative to the wearer's head, usually by moving the head mounting means. Preferably, the movement of the seal will be provided with a minimal adjustment in order to change from the free to the sealed condition.

The various types of seal may be used according to the present invention. For example, the seal may be any one of the following list or a combination of the following types of seals, such list to be non-exhaustive:

a differential pressure seal, which maintains the seal with the wearer's face due to a pressure differential;

a silicon (or similar material) seal;
gel/latex/silicon seal; or
a deployable seal using deploying mechanisms to deploy or moved the seal between the free and sealed condition.

In embodiments where a silicon or a gel seal is used, the seal will preferably have a shape memory. Indeed, in preferred embodiments, the seal, regardless of type, will have a shape memory.

According to one particularly preferred embodiment, the seal may be mounted relative to the lens(es) with the lens(es) movably mounted to the frame. A mechanism is typically provided to move the lens(es) relative to the frame, towards and away from the wearer's face.

According to a further preferred embodiment, the frame of the eyewear of the present invention may have a seal overmoulded. In particular, the front of the frame which supports the lenses will typically have a pair of eye frame or rim portions which substantially surround a wearer's eye and are adapted to abut the user's face about their eye or eye socket. Preferably, the eye frame portions will be overmoulded with a resilient material in order to form a seal with the lens at the front. A rear portion of the seal may be provided in order to seal against the user's face when worn in the substantially fluid tight condition.

The preferred rear seal is a resilient extension which will preferably extend rearwardly from the frame seal and may have a depending portion extending either upwardly or downwardly in order to abut the user's face. Preferably, the rear seal will be highly compressible. One or more vent openings may be provided in the rear seal, these vent openings unobstructed when the eyewear is in the free condition but when the rear seal is preferable deformed during movement to the substantially fluid tight condition, the vent openings will typically be closed, normally due to the deformation of the resilient material used to form the seal. The rear seal typically extends circumferentially about each eye frame or rim.

According to a most preferred embodiment, the eyewear will be provided with both an adjustment strap and a pair of earstems. Normally the earstems and the adjustment strap will engage with one another to allow the eyewear to assume the free and substantially fluid tight conditions.

The adjustment strap will normally be resilient and may be provided with a limited deformability. Stress inducing portions may be provided in the adjustment strap to allow the adjustment strap to flex and therefore be folded.

The adjustment strap will typically include a portion adapted to extend about the rear of the user's head and a pair of free end portions adapted to engage with each earstem in order to connect the adjustment strap to the earstems. Normally, the adjustment strap will be connected to the earstems in adjustable fashion. For example, each free end of the adjustment strap may be provided with one or more openings spaced over its length which may engage with an extension portion associated with each of the earstems. By moving the adjustment strap to an opening closer to the free end, the adjustment strap can be lengthened.

Preferably, each earstem may be provided with a locking means in order to releasably lock the free end of the adjustment strap to the earstem. In this configuration, the earstems will preferably be hollow, at least at the rear end. Preferably, the locking means will include a trigger which is accessible from the outside of the earstem, located in opening in the earstem, and which, when depressed, can move within the hollow earstems to be drawn rearwardly to attach the adjustment strap. On a portion of the trigger, but within the hollow earstems, will typically be an extension portion to engage with the openings in the free end of the adjustment strap.

The trigger will typically be biased outwardly through provision of a spring-loaded portion adapted to force or bias the trigger outwardly unless sufficient force is provided to overcome the spring-loaded portion.

Guides may be provided in order to govern the movement of the trigger portion during actuation to release the adjustment strap. The trigger portion may be completely removable from the hollow earstems or may be extendable and retractable but not completely removable from the earstems. Typically, a locking trigger is provided on each earstem with the trigger actuable from the outside of the earstems.

A tension portion may be provided between the forward end of the rear trigger and extending forwardly to releasably engage with a tab member either attached to or integrally formed with the lens and which extends rearwardly through the eye rim and seal. The tension portion will preferably be fixed to the earstem along its length to define a forward tension strap portion and a rear tension strap portion. Alternatively, two separate tension portions may be provided. This allows the forward and rearward triggers to be operated independently of each other. The respective tension portions are biased toward the fixing or mid-point.

The tension portion will be the controlling member or portion for the actuation of the eyewear into the different conditions.

In use, the user will typically prime the rear trigger portion, by drawing the rear adjustment strap rearwardly. This will loosen the rear adjustment strap and engage the rear trigger in the rear or locking opening against the biasing force of the rear tension strap portion. The rear trigger portion is then locked to the earstem again, and the resilience of the rear tension strap portion will act to tighten the adjustment strap should the rear trigger portion be depressed, freeing the trigger portion. In this condition, the trigger portion may move such that the trigger portion is received within the earstem forwardly of the rear locking opening which tightens the adjustment strap.

Similarly, the forward trigger portion is also typically primed by drawing the eye rims and/or lens forwardly against the biasing force of the forward tension strap portion. The forward trigger portion is then locked to the earstems again, using the forward locking opening. The forward trigger may be depressed and it may be received within the earstem but more rearwardly of the forward earstem opening due to the biasing force of the forward tension strap portion. When released, through depression, the forward trigger moves rearwardly through the earstems, under the biasing force of the forward tension strap portion and moves the eyewear the substantially fluid tight condition.

According to a preferred embodiment, flexible attachment means are preferably attached to the lens(es) and pass through or over the frame, end pieces and earstems of the eyewear.

Alternative tightening/loosening means may be provided, typically on the end pieces or earstems. As the flexible attachment means tightened, the lens(es) with the seal is preferably moved into the sealed condition with the seal abutting the wearer's face and forming the seal therewith.

The tightening/loosening means will typically be independent of each other so that the lenses can be adjusted individually (if more than one lens is provided) or so that each side of a monolithic lens can be adjusted separately to take into account any non-symmetrical shape of the wearer's face. Alternatively, the flexibility of the frame itself may provide sufficient adjustment capability in order that individual lens adjustment means are not necessary.

A further alternative adjustment mechanism may be a tightening system whereby the adjustment strap can be tighten/loosened with a rotatable spool. The strap or a portion of the strap is threaded through a series of opposing guide members positioned on the frame or the earstems of the eyewear. The strap and guide members preferably have low friction surfaces to facilitate sliding of the strap along the guide members so that the strap evenly distributes tension across the eyewear. The tightening mechanism allows incremental adjustment of the tension of the strap. A release mechanism allows a user to quickly loosen the strap.

A rotatable spool for receiving a strap is provided, the spool rotatable in a first direction to take up strap and a second direction to release the strap. A knob is connected to the spool such that the spool can be rotated in the first direction in response to rotation of the knob. A releasable lock is provided for preventing rotation of the spool in the second direction. Releasing the lock permits the spool to rotate in the second direction in response to tension the strap, but the spool is not rotatable in the second direction in response to rotation of the knob. In one embodiment, the knob is only rotatable in the first direction.

According to an embodiment, the lens(es) will typically be more arcuate in order to space the lens(es) from the wearer's eye particularly in the sealed condition.

The frame of the eyewear of the present invention is typically held relative to a wearer's face by a head mounting means. Either the lens or the frame is mounted for movement relative to the wearer's head. The lens(es) may be mounted for movement relative to the frame such that as the frame is drawn rearwardly towards the wearer's face, the lens remains spaced from the wearer's eyes.

The above deploying mechanism is only one of such mechanisms that can be used. Other mechanisms for example include mounting the seal relative to the frame of the aisle where using one or more movable arms and with the wearer able to move the arms, whether directly or indirectly, and thereby the seal, between the sealed and free conditions.

Of course, the seal, or deployable mechanism may be biased into one or the other of the free or sealed conditions.

According to an alternative preferred embodiment, a configuration can be provided that allows the head strap to form a portion of the tensioning mechanism.

According to this embodiment, the ear stems provided are preferably arcuate to match the contours of the side of wearer's head. Each ear stem is typically provided with a channel therein, normally an outwardly facing channel. The channel is preferably shaped and in use, preferably receives a portion of the head strap.

According to a particularly preferred embodiment, the channel is typically elongate and extends rearwardly to the (rear) end of the ear stem being shaped to receive the head strapped closely within the channel so as to confine the head strap, allowing elongation in a rearward direction only.

A forward portion of the channel on each ear stem is preferably provided with an enlarged opening in order to at least partially receive an enlarged head of the head strap. The shaped forward portion will typically constrain the enlarged head of the head strap to allow elongation of the head strap to create a biasing force within the head strap.

Normally, each ear stem is provided with a mounting point for pivotally mounting an extender portion relative to each respective ear stem.

The head strap of this preferred embodiment is typically resilient and has dual functionality being provided as a part of the tensioning mechanism used to drive the frame into the sealed condition and also for normal use as a head strap to hold the eyewear to a person's head. Normally, the eyewear will be worn with the head strap in the extended or primed condition but closely against the user's head in order that a relatively minor shortening of the head strap will drive the eyewear, and particularly the frame of the eyewear, into the sealed condition against the user's head.

The head strap on this embodiment is preferably unitary and is attached to the respective ear stem on either side of the eyewear through engagement of the enlarged head portion of the head strap with the shaped opening provided in the ear stem. The head strap is preferably elongate and will typically be substantially planar.

The enlarged head portion will be shaped to abut or otherwise engage one or more shoulders on the earstem to retain and positively locate the enlarged head portion. In particular, the sides of the enlarged head portion may abut the sides of the enlarged opening in the channel. Further, the enlarged head portion may have a shoulder on the rear surface to engage a corresponding shoulder in the enlarged opening in the channel.

The head strap will also preferably be attached to an extender portion which is movable relative to the ear stem. Normally, the head strap is attached to the extender portion towards the rear of the extender portion which will normally be located adjacent the rear of the ear stem.

The head strap will preferably be located in the channel in the respective ear stem between the ear stem and the extender portion.

The head strap will normally be manufactured of a gel, rubber, silicone or similar type of material having good resilient properties which will also assist with making the head strap comfortable for use when worn.

The extender portion will normally be shaped, and preferably will be arcuate when viewed in plan. It is particularly preferred that the shape of the extender portion corresponds to a least a part of the shape of the ear stem relative to which the extender portion is mounted.

The extender portion will preferably be received at least partially within an outer portion of the ear stem in order to allow guided movement of the extender portion. The movement of the extender portion relative to the ear stem will preferably be reciprocal in a forward and rearward direction.

The extender portion is normally attached to the head strap such that extension of the head strap draws the extender portion rearwardly relative to the ear stem. Any attachment mechanism may be used and normally, the attachment mechanism is provided at a rear of the extender portion in order to attach to the head strap.

A forward portion of the extender portion, and normally an outer side of the extender portion is provided with at least part of the latching mechanism in order to temporarily retain the head strap in the extended, elongated or primed condition against the bias of the head strap.

One simple mechanism which could be used to latch the extender portion is to provide the extender portion with a number of abutment shoulders against which a catch located on the trigger arm can abut. Normally, a number of equally spaced abutment shoulders are provided over a portion of the length of the extender arm in order to provide different biasing forces.

The configuration of this embodiment also typically includes a trigger arm. The trigger arm is provided for the dual purposes of latching against the extender portion in order to hold the head strap in the elongate or primed condition, and also to provide a trigger to release the extender portion and the head strap as required to allow the bias of the head strap to move the eyewear and particularly the frame, into the sealed condition against a user's face or head.

Preferably, the trigger arm is arcuate in shape when viewed in plan having a forward trigger portion and a rearward catch portion. The rear catch portion is typically provided to engage with an abutment shoulder on the extender. The catch portion is normally rectangular in cross-section in order to provide a secure abutment with the shoulder. Typically however the shape of the catch portion corresponds to the shape of the abutment shoulder and therefore can have any shape including being angled.

The trigger arm is mounted for pivotal movement relative to the ear stem. Preferably, the trigger arm is mounted directly to the ear stem about a pivot pin or point. The forward and rearward portions of the trigger arm are typically defined according to the location of the pivot point.

Preferably, the pivot is provided as a pair of spaced apart arms extending substantially transversely from the trigger arm on either side (upper and lower) of the head strap, which are mounted to the ear stem. Normally, the ear stem will be provided with a depression or opening into which a protrusion extending from the spaced apart arms or a portion of the spaced apart arms themselves, is at least partially received allowing the trigger arm to pivot thereabouts.

The forward portion of the trigger arm will typically overlie the enlarged head of the head strap. Normally, a forward portion of the trigger arm will abut the enlarged head portion of the head strap. Due to the resilience of the head strap and the head portion of the head strap, the trigger arm will be biased by the head portion into the engaged condition about a pivot. Depression of the forward portion of the trigger arm against the enlarged head portion of the head strap, typically deforms the enlarged portion of the head strap in order to allow depression of the trigger portion. This preferably releases or disengages the abutment of the catch and allows the head strap to shorten under the resilient bias in order to draw the eyewear and particularly the frame of the eyewear, against the user's head to the sealed condition.

Typically, the trigger portions on both sides of the eyewear are activated at the same time to release the head strap to provide balanced sealing.

Alternatively, the head strap can be fixed on one side and have a trigger mechanism substantially as described above provided on one side only in order to allow one-handed activation.

Therefore, the head strap of this particular embodiment forms a return spring portion for the trigger arm as well as providing a part of the tension mechanism to draw the eyewear and particularly the frame, into the sealed condition against the user's head or face.

BRIEF DESCRIPTION OF THE DRAWINGS

Various embodiments of the invention will be described with reference to the following drawings, in which.

DETAILED DESCRIPTION OF THE PREFERRED EMBODIMENT

Figure 1:
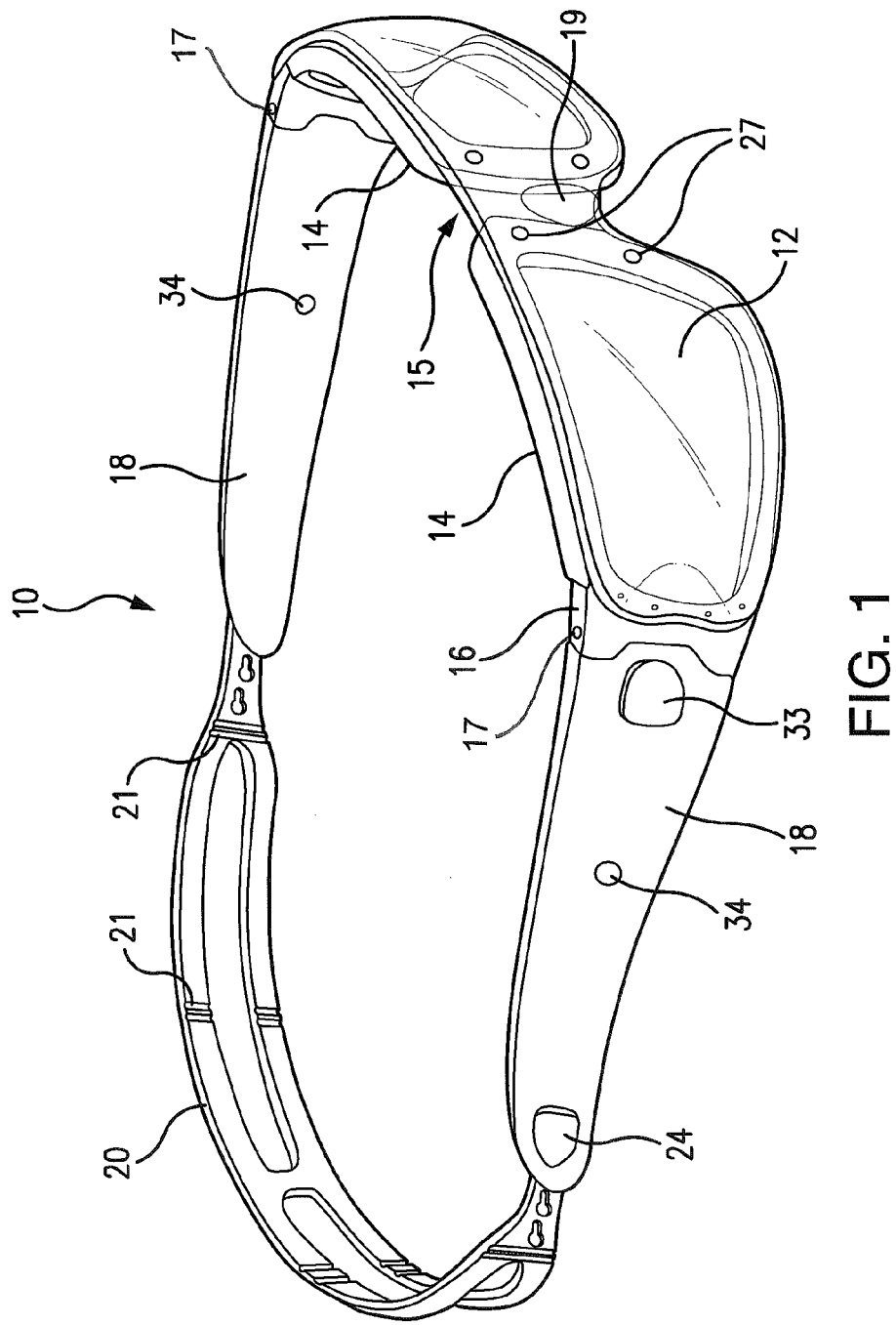
FIG. 1 is a partially exploded, schematic view of eyewear according to one embodiment of the present invention.

According to one embodiment of the present invention illustrated in FIG. 1, eyewear in the form of sunglasses 10 is provided.

Figure 3:
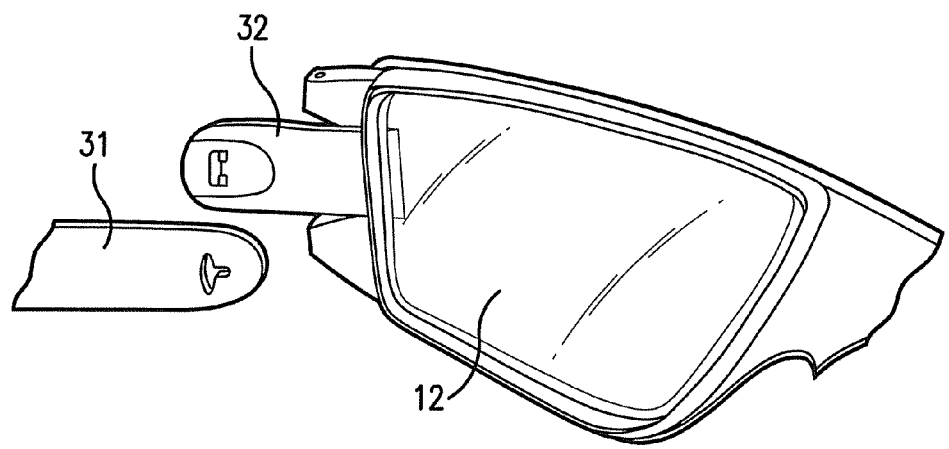
FIG. 3 is a detailed view of the connection mechanism between the strap and the forward frame according to a preferred embodiment.
Figure 7:
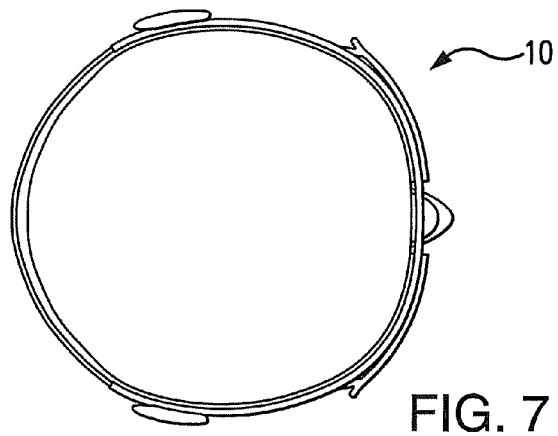
FIG. 7 is a view from above of the eyewear as worn by user in the glasses configuration.
Figure 9:
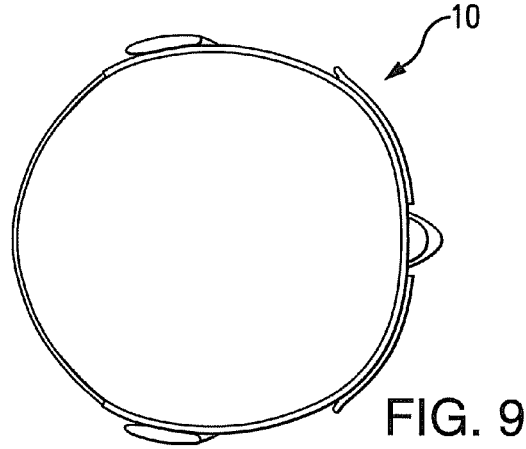
FIG. 9 is a view from above of the eyewear as worn by user in the goggles configuration.

According to the illustrated embodiment, the sunglasses 10 are adapted to provide a substantially fluid tight seal about the wearer's eyes. The illustrated sunglasses 10 include a monolithic lens 12, as illustrated in FIG. 3, for positioning in front of a wearer's eyes. The frame of the illustrated embodiment includes a pair of eye rims 14, each attached to an earstem 18, and the eye rims are connected to each other by the monolithic lens 12. The sunglasses 10 also include a head mounting strap to attach the frame relative to a wearer's head as illustrated in FIGS. 7 and 9 particularly.

Rear seals 13 are attached relative to each eye rim and located about a periphery of the wearer's eyes so that the sunglasses 10 are wearable in a substantially fluid tight condition in which the rear seals 13 form a substantially fluid tight seal about the wearer's eyes, and a free condition in which the sunglasses 10 are wearable with the rear seal 13 spaced from the wearer's eyes.

The present invention relates to eyewear having multiple functions, including being usable as traditional sunglasses, as air/water tight goggles, with the lenses thereof also being capable of providing sun protection for the wearer.

The frame of the eyewear of the illustrated embodiment is at least partially rigid and includes the following components:

Eye wires (rims) 14: Part of the frame front into which the lenses are inserted.

Bridge 15: The area between the lenses that extends over the nose and supports the majority of the weight of the sunglasses. In the illustrated embodiment, the monolithic lens itself forms the bridge.

End pieces 16: Extensions of the frame front to which the temples are attached.

Hinges 17: Part of the frame that connects the frame front to the temples and allows the temples/earstems to swing.

Temples/earstems 18: Parts of the frame that extend over and/or behind the ears to help hold the frame in place.

Nose pads 19: Plastic pieces that may be attached directly to the frame or to pad arms. They help keep the frame in its proper position.

Plastics or composite materials are preferred materials of construction given the use of the eyewear of the present invention in water and other hostile environments.

The frame of the present invention is at least partially rigid. The frame portions including the frame front, including the end-pieces and the earstems as well is sufficiently strong but deformable upon application of a sufficient force. The frame and lens(es) should be flexible enough to conform readily to the profile of a user's face.

The frame of the eyewear of the illustrated embodiment has a seal 26 overmoulded over the eye rims. The eye rims 14 support the lens 12 and substantially surround a wearer's eye and are adapted to abut the user's face about their eye or eye socket. The eye rims 14 of the preferred embodiment are overmoulded with a resilient material in order to form a seal with the lens 12 at the front, each lens 12 being attached to the eye rims 14 using screws 27 in the illustrated embodiment. The lens 12 simply abuts the front of the eye rim 14 and is secured there with the overmoulded seal 26 between the eye rim 14 and the lens 12.

A rear seal 13 is provided on the in order to seal against the user's face when worn in the substantially fluid tight condition.

Figure 5:
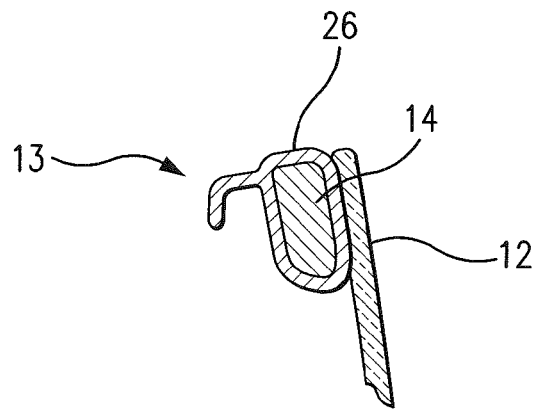
FIG. 5 is a detailed sectional view of the lens with the seal according to a particularly preferred embodiment.

The rear seal 13 illustrated in FIG. 5 is integrally moulded with the overmoulded seal 26 and has a resilient extension which extends rearwardly from the overmoulded seal about the periphery of the eye rim 14 and has a depending portion extending downwardly in order to abut the user's face. The rear seal is highly compressible.

Figure 12:
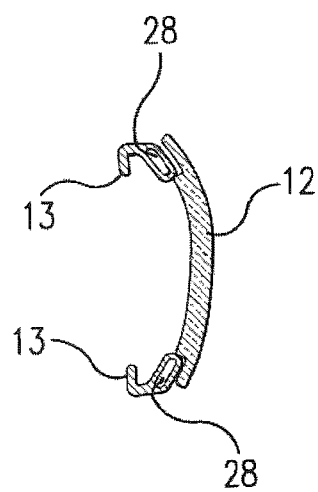
FIG. 12 is a sectional side view of the frame with a lens attached thereto according to a preferred embodiment.

As illustrated in FIG. 12, a vent opening 28 is provided in the rear seal 13 on each eye rim 14, the vent openings 28 unobstructed when the eyewear is in the free condition but when the rear seal 13 is deformed during movement to the substantially fluid tight condition, the vent openings 28 are closed, normally due to the deformation of the resilient material used to form the seal.

According to a most preferred embodiment, the eyewear is provided with both an adjustment strap 20 and a pair of earstems 18. Normally the earstems 18 and the adjustment strap 20 engage one another to allow the eyewear to assume the free and substantially fluid tight conditions.

The illustrated adjustment strap 20 is resilient and is provided with a limited deformability. Stress inducing portions 21 may be provided in the adjustment strap 20 to allow the adjustment strap 20 to flex and therefore be folded.

Figure 2:
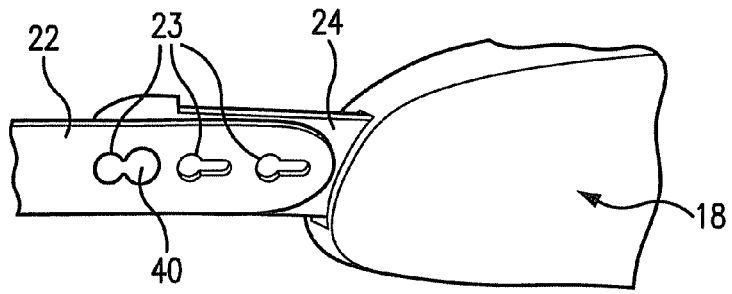
FIG. 2 is a detailed view of the connection mechanism between the strap and the earstem according to a preferred embodiment.
Figure 4:
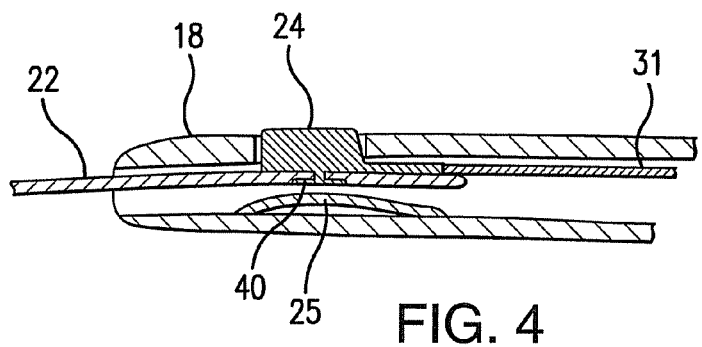
FIG. 4 is a detailed sectional view of the connection mechanism illustrated in FIG. 2.

The illustrated adjustment strap 20 includes a portion adapted to extend about the rear of the user's head and a pair of free end portions 22 (best illustrated in FIGS. 2 and 4)

adapted to engage with each earstem 18 in order to connect the adjustment strap 20 to the earstems 18. Normally, the adjustment strap 20 is connected to the earstems in an adjustable fashion. For example, each free end 22 of the adjustment strap 20 illustrated in FIGS. 2 and 4 is provided with multiple openings 23 spaced over its length adapted to engage with an extension portion associated with each of the earstems 18. By moving the adjustment strap 20 to an opening 23 closer to the free end, the adjustment strap 20 can be lengthened.

Each earstem of the illustrated embodiment is provided with a rear locking means in order to releasably lock the free end of the adjustment strap to the earstem. In this configuration, the earstems 18 are hollow at least at the rear end. Preferably, the locking means will include a rear trigger portion 24 which is accessible from the outside of the earstem 18 located in a rear locking opening 29 in the earstem 18 and which when depressed, can move within the hollow earstems 18 and can be drawn rearwardly, as illustrated in FIG. 2 to adjust the length of the rear adjustment strap. On a portion of the rear trigger 24 but within the hollow earstems 18 is an extension portion 40 to engage with one of the openings 23 in the free end of the adjustment strap 20 to adjust the length of the strap 20.

The rear trigger 24 is biased outwardly through provision of a spring-loaded portion 25 adapted to force the trigger 24 outwardly unless sufficient force is provided to overcome the spring-loaded portion 25.

Figure 6:
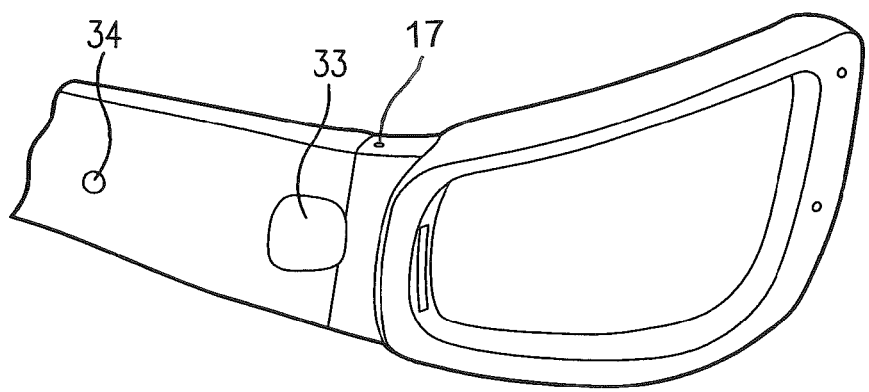
FIG. 6 is an isometric view of the forward frame showing the overmoulded seal used according to a preferred embodiment.

Typically a rear locking trigger 24 and a forward locking trigger 33, as illustrated in FIG. 6, is provided on each earstem 18 with each trigger actuable from the outside of the earstems 18. The forward trigger 33 is biased outwardly through provision of a spring-loaded portion 25 adapted to force the trigger 33 outwardly unless sufficient force is provided to overcome the spring-loaded portion 25. Further, the rear locking trigger is biased towards the front of the eyewear and the forward locking trigger is biased toward the rear of the headwear.

According to the illustrated embodiment, a tension strap 31 is provided between the forward end of the rear trigger 24 and extending forwardly to releasably engage with a tab member 32 either attached to or integrally formed with the lens 12 and which extends rearwardly through the eye rim 14. The tension strap 31 is fixed to the earstem along its length with a rivet 34 to define a forward tension strap portion and a rear tension strap portion. This allows the forward 33 and rearward 24 triggers to be operated independently of each other. The respective tension portions are biased toward the rivet 34.

The tension strap is the controlling member or portion for the actuation of the eyewear into the different conditions.

In use, the user will typically prime the rear trigger portion 24, by drawing the rear adjustment strap 20 rearwardly. This will loosen the rear adjustment strap 20 and engage the rear trigger 24 in the rear or locking opening 29 against the biasing force of the rear tension strap portion. The rear trigger portion 24 is then locked to the earstem 18 again, and the resilience of the rear tension strap portion acts to tighten the adjustment strap 20 should the rear trigger portion 24 be depressed. In this condition, the rear trigger portion 24 may be depressed again such that the trigger portion 24 clears the locking opening 29 and is received within the earstem 14 forwardly of the rear locking opening 29 which tightens the adjustment strap 20.

Similarly, the forward trigger portion 33 is also typically primed by drawing the eye rims 14 and/or lens 12 forwardly against the biasing force of the forward tension strap portion. The forward trigger portion 33 is then locked to the earstems 18 again, using the forward locking opening 30. The forward trigger 33 may be depressed and is then received within the earstem 18 but more rearwardly of the forward earstem opening 30 due to the biasing force of the forward tension strap portion. When released, through depression, the forward trigger 33 moved rearwardly through the earstems 18, under the biasing force of the forward tension strap portion and moves the eyewear the substantially fluid tight condition.

Figure 8:
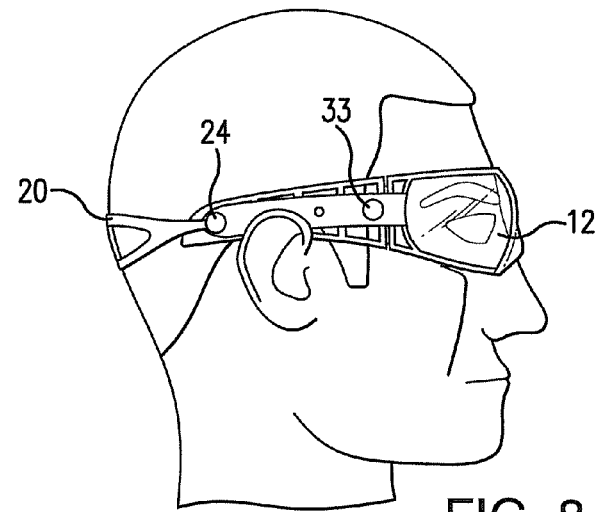
FIG. 8 is a side view illustrating the eyewear as worn by user.
Figure 10:
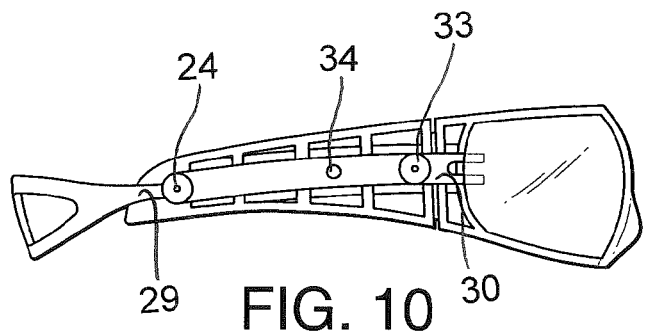
FIG. 10 is a side view of the eyewear of a preferred embodiment in the locked condition.
Figure 11:
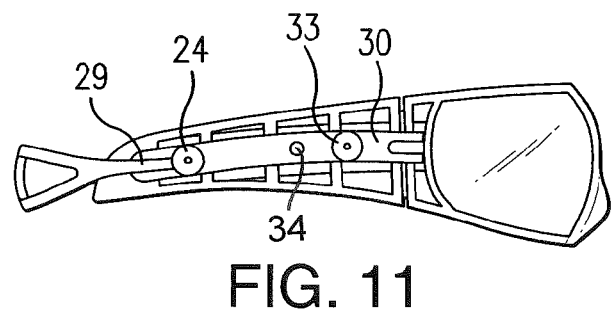
FIG. 11 is a side view of the eyewear of a preferred embodiment in the free condition.

Therefore, the primed condition illustrated in FIGS. 7, 8 and 10 of each of the trigger portions is an extended position against the biasing force of the tension strap. Depression of the rear trigger releases the adjustment strap to achieve a tightened condition and depression of the forward trigger releases the eye rims to assume the substantially fluid tight condition. The free conditions (after depression) are illustrated in FIGS. 9 and 11.

The seals are movable between the free and sealed conditions. Preferably, this movement is provided by moving either the seal relative to the frame, or, the seal may be provided in a fixed relation to the frame and the frame may be moved relative to the wearer's head, usually by moving the head mounting means. Preferably, the movement of the seal will be provided with a minimal adjustment in order to change from the free to the sealed condition.

In the illustrated embodiment, the seal has a shape memory.

Figure 16:
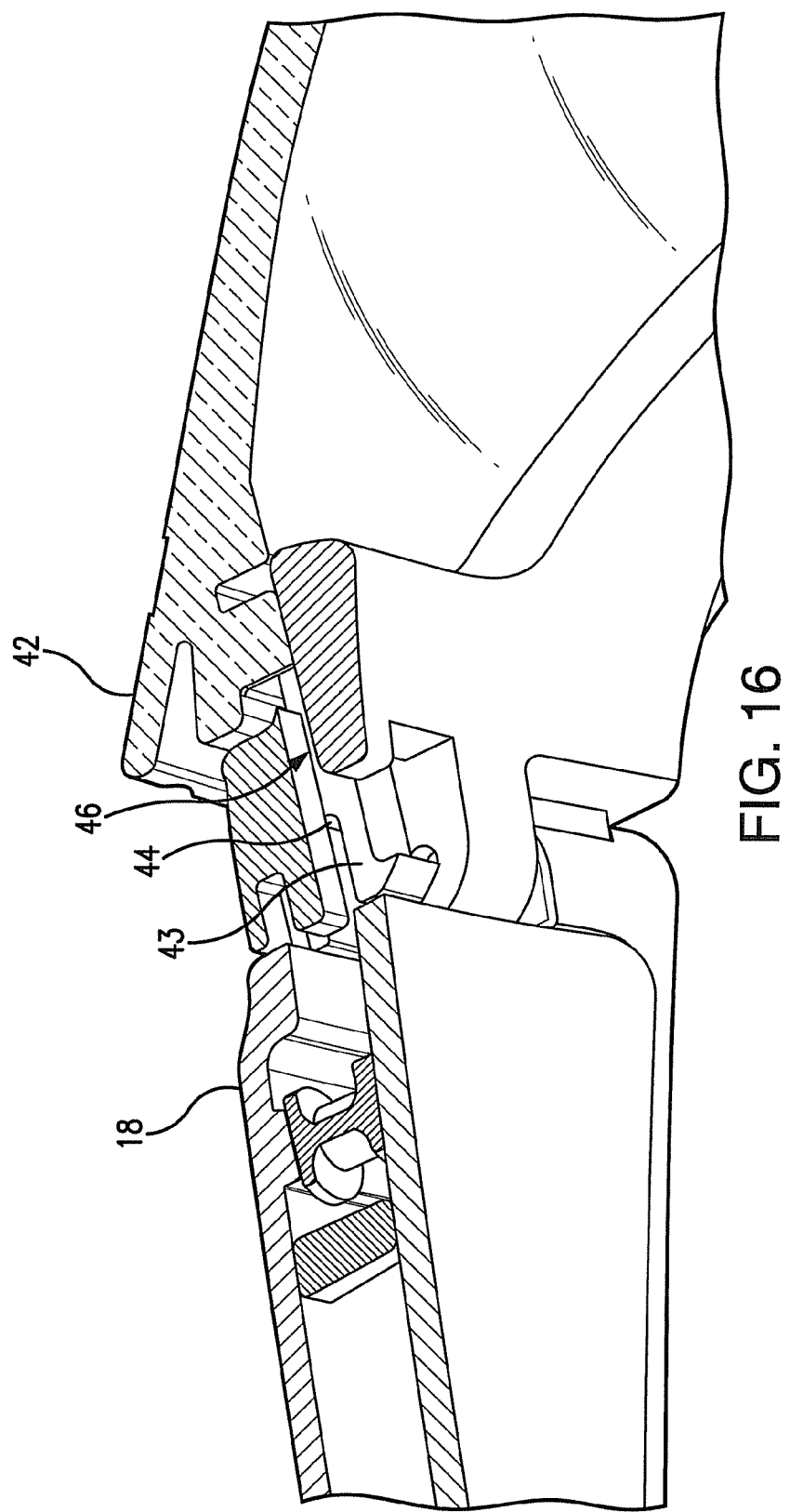
FIG. 16 is a sectional view of the embodiment illustrated in FIG. 15 along line A-A with the lens in the sealed condition.
Figure 17:
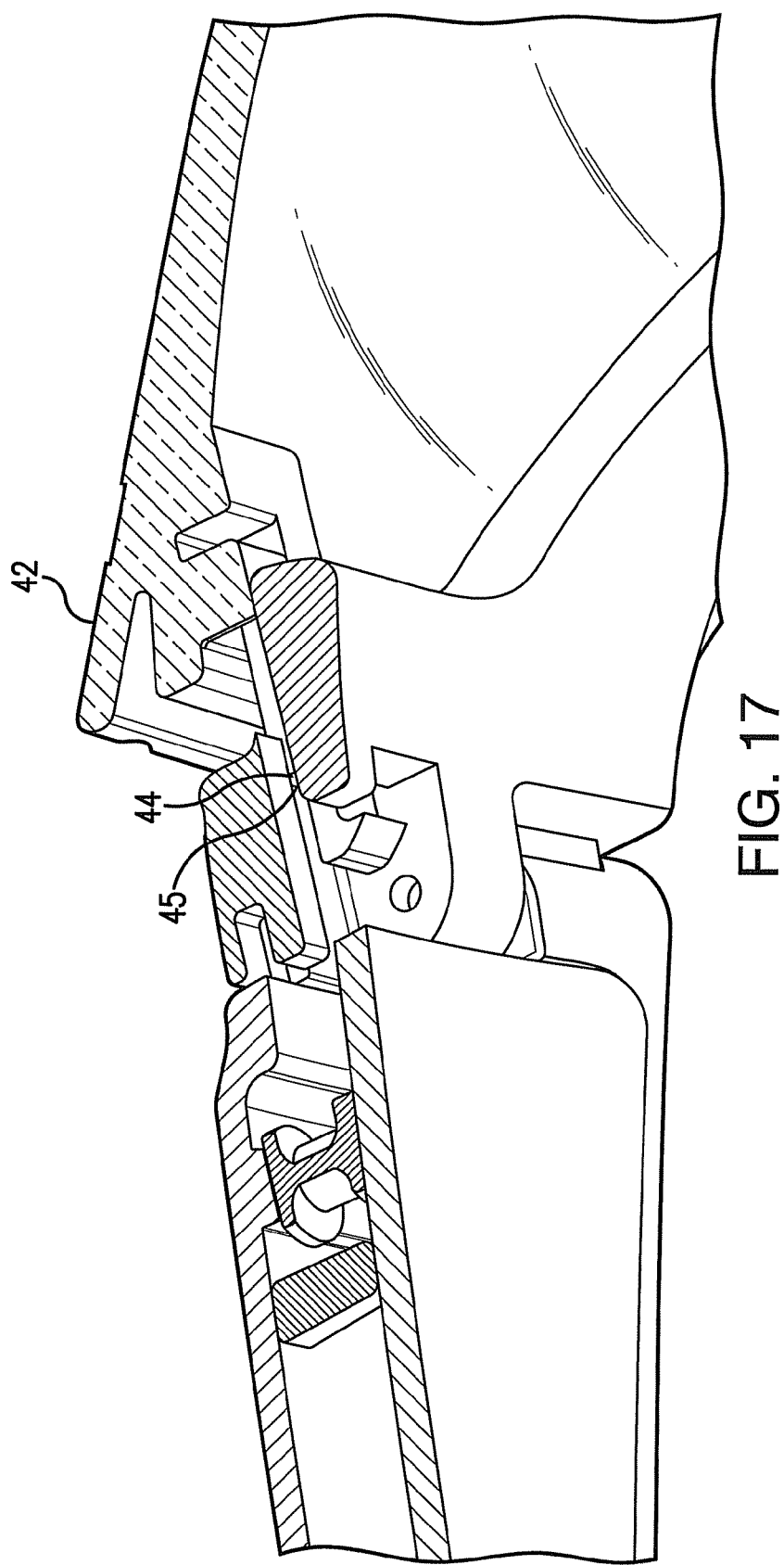
FIG. 17 is a is a sectional view of the embodiment illustrated in FIG. 15 along line A-A with the lens in the unsealed or free condition.

In an alternative embodiment illustrated in FIGS. 16 and 17, an optional feature of providing a releasable seal between the lenses 12 of the eyewear and the rims 14 of the frame of the eyewear is provided.

The lens 12 of this embodiment is typically hinged to the frame at hinge points 41, normally toward the nose bridge of the eyewear. The rear of the lens 12 is typically shaped to correspond to the frame and a peripheral portion of the lens overlies the frame. The lens 12 is moveable between a sealed condition in which the lens is sealed to the frame and a free condition in which the lens 12 is not sealed to the frame. A sealing member may be provided about the frame and/or rear of the lens between the frame and the lens and/or between the frame and the user's face.

The lens 12 is preferably provided with a lateral extension 42 which acts as a gripping or depression portion. This portion (marked in the drawings with the word "push") is associated with an extension 43 which is releasably engageable with a portion of the frame or earstem to move the lens 12 between the sealed and unsealed conditions. Typically the lens 12 is biased into the sealed condition.

The extension 43 preferably has a shoulder 44 and the frame or earstem is provided with an abutment shoulder 45 such that the lens 12 may be pulled forwardly (using the lateral extension 42) which moves the respective portions to allow the shoulder 44 of the extension 43 and the abutment shoulder 45 of the frame or earstem to engage one another, when released under the bias of the lens 12. This will typically hold the lens 12 in the unsealed condition. Depressing the lateral extension 42 rearwardly (and preferably inwardly) disengages the shoulder 44 from the abutment shoulder 45 returning the lens 12 to the sealed condition under the bias of the lens 12.

The extension 43 is preferably elongate and typically slides within a channel or opening 46 provided in the frame, which guides the movement. The extension 43 is preferably biased into the unsealed position which results in more or less automatic engagement with the abutment shoulder 45 when moved into the correct position. The bias of the extension 43 must therefore be overcome prior to movement of the lenses 12 into the sealed condition.

Typically, the abutment shoulder 45 is provided laterally outside the extension 43 and the extension 43 is biased outwardly. Movement of the extension 43 inwardly using the lateral extension 42 of the lens 12 is required to allow movement of the lens 12 to the sealed condition.

To create ventilation in and around the lens 12, the lateral extension 42 of the lens 12 (where it has the indentations behind the "push" label) is pulled forward and the shoulder or barb holds the lens away from the sealed frame. To seal the frames again the barb is overcome by pushing the lenses in again with a motion toward the centre of the wearer's head at the point marked "push".

Figure 18:
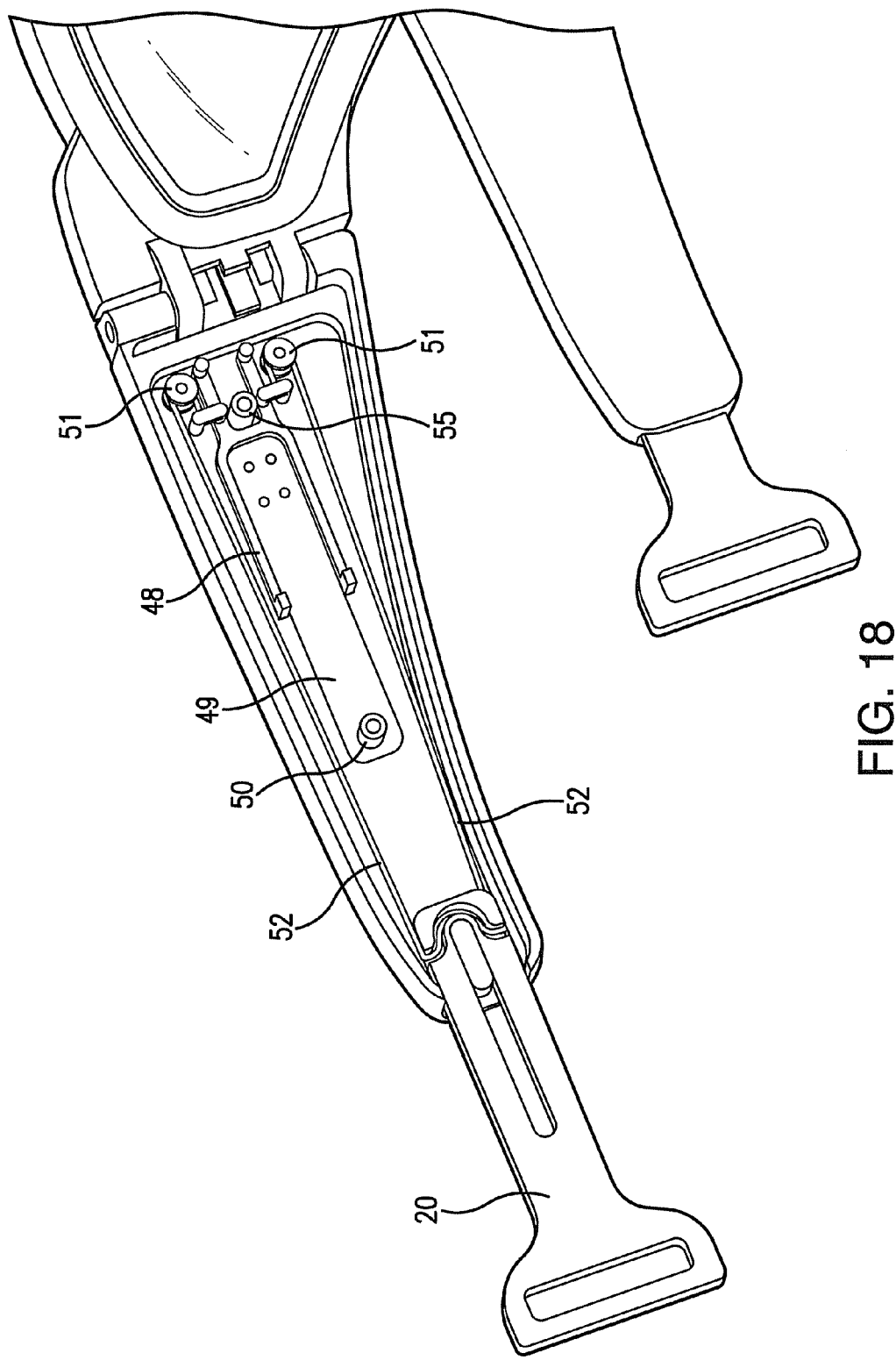
FIG. 18 is a detailed view of an earstem of the embodiment illustrated in FIG. 13 with the cover removed and showing the trigger assembly in the primed condition which is also the free condition.
Figure 19:
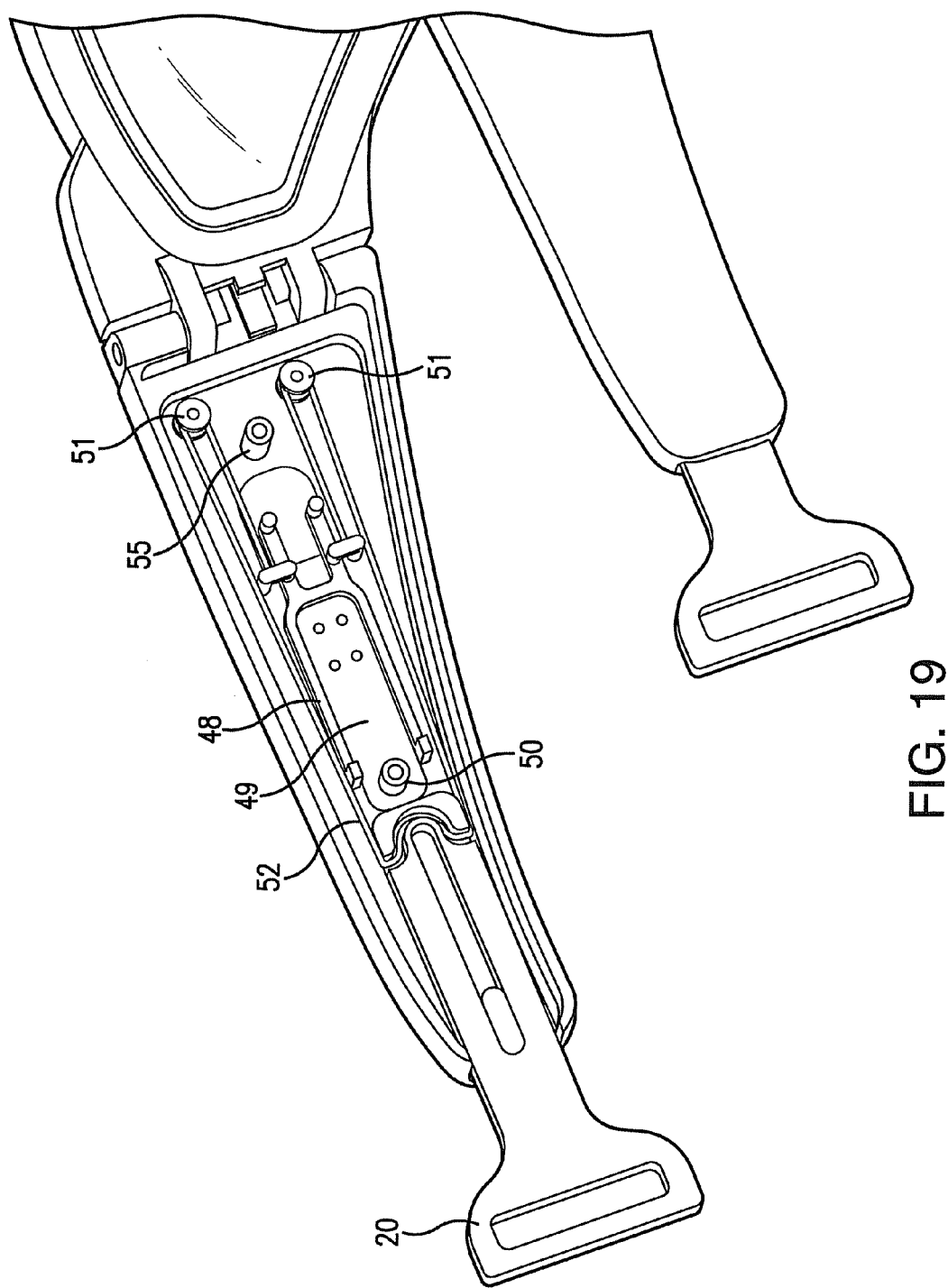
FIG. 19 is a detailed view of an earstem of the embodiment illustrated in FIG. 13 with the cover removed and showing the trigger assembly in the activated condition which is also the sealed condition.

In an alternative embodiment illustrated in FIGS. 12 to 19 but particularly FIGS. 17 and 18, the strap 20 is provided in association with the frame to move the frame between a sealed condition against a wearer's face and a free condition in which the frame is not sealed against the wearer's face. A trigger mechanism is preferably mounted on each earstem 18 and a tension mechanism is provided in association with the trigger mechanism.

The trigger mechanism will preferably include a release button 47 or similar accessible from outside the earstem to trigger actuation of the tension mechanism to move the frame into the sealed condition against a wearer's face. The earstem 18 is preferably hollow and contains other components actuable by the release button.

The trigger mechanism is associated with a locking assembly for temporarily locking the strap into the free condition.

The locking assembly typically includes a locking body 48 associated with the head strap 20, normally through a resilient portion 49 which undergoes forced temporary deformation (lengthening) during the priming step. Triggering release of the locking assembly allows the natural bias of the resilient portion 49 to assert itself and moves the strap 20 into the sealed condition.

The locking body 48 will typically be robustly attached or formed with the resilient portion 49. The resilient portion 49 will preferably be mounted relative to the earstem and normally to a fixed point 50 along the earstem in order to be forcibly deformed against that fixed point 50.

The locking body 48 is preferably attached to the strap 20 via one or more pulley components 51 which allow extension of the strap 20 when the locking body 48 is in the primed condition. The pulley components 51 are preferably provided towards a forward end of the earstem. Normally there will be two pulley components 51 to better balance the mechanism.

The strap 20 is attached to one or more elongate, and substantially inextensible fibre members 52 which extend from the strap 20 forwardly about the pulley components 51 and then rearwardly again to the lock body 48.

Due to this configuration, drawing the strap 20 rearwardly during priming will force the lock body 48 forwardly against the biasing force of the resilient portion 49.

One or more catch elements are provided in the earstem and mounted to the earstem to engage the lock body 48 when moved to the primed condition. It is preferred that the catch elements include a ramp portion with a catch edge and the lock body 48 includes a corresponding shoulder such that the lock body 48 can slide relative to the catch elements until the shoulder engages with the catch edge. Normally the ramp portion will extend toward an inner side of the earstem (closer to the head of the user) and the catch edge will be provided at a forward portion (towards the front of the earstem). Again, normally a pair of opposed catches and at least one shoulder will be provided to provide balance to the mechanism.

The trigger button 47 of the trigger mechanism will preferably be associated with a portion of the lock body 48 adjacent the shoulder, and is normally biased outwardly. Depression of the trigger button 47 will normally displace the shoulder of the lock body, disengaging the shoulder from the catch element and allowing the natural bias of the resilient portion 49 to assert itself and move the strap 20 into the sealed condition.

Alternatively, the lock body 48 may be provided with a shoulder defining the button 47. The shoulder of the button 47 may engage with a rear periphery of an opening in the earstem when the mechanism is primed. Depression of the button will disengage the shoulder from the periphery and allow movement of the strap relative to the earstem.

In an alternative embodiment, the fibre elements may be resilient and the resilience of the fibre components can be used as the resilient portion which undergoes forced temporary deformation (lengthening) during the priming step.

The tension mechanism is preferably biased into a tightened condition and is primed when the trigger mechanism is engaged and adapted to tighten the rear adjustment strap 20 when the rear trigger mechanism is actuated.

Figure 13:
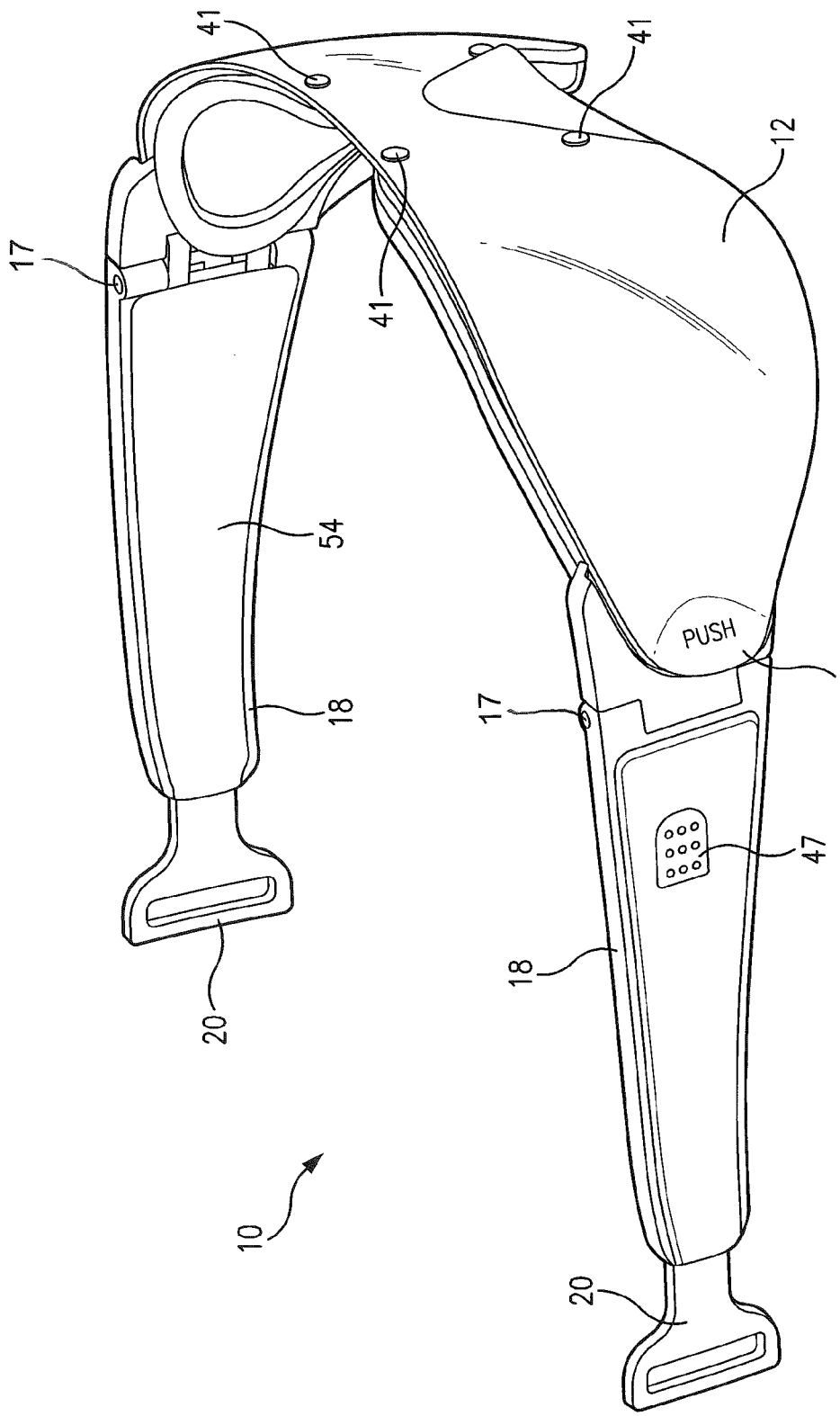
FIG. 13 is an axonometric view of eyewear according to a further preferred embodiment of the present invention.
Figure 14:
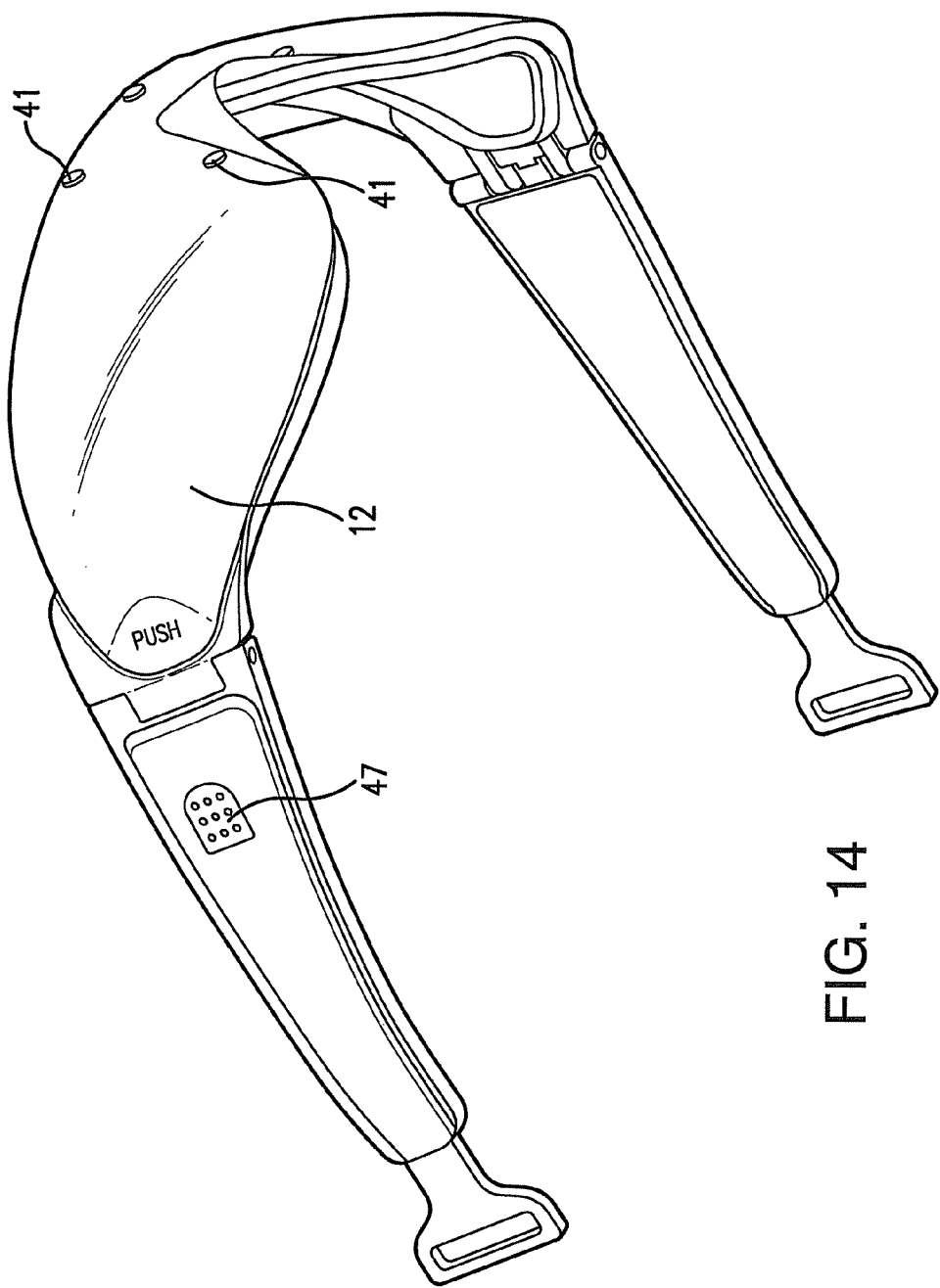
FIG. 14 is a view from below of eyewear according to the embodiment illustrated in FIG. 13.
Figure 15:
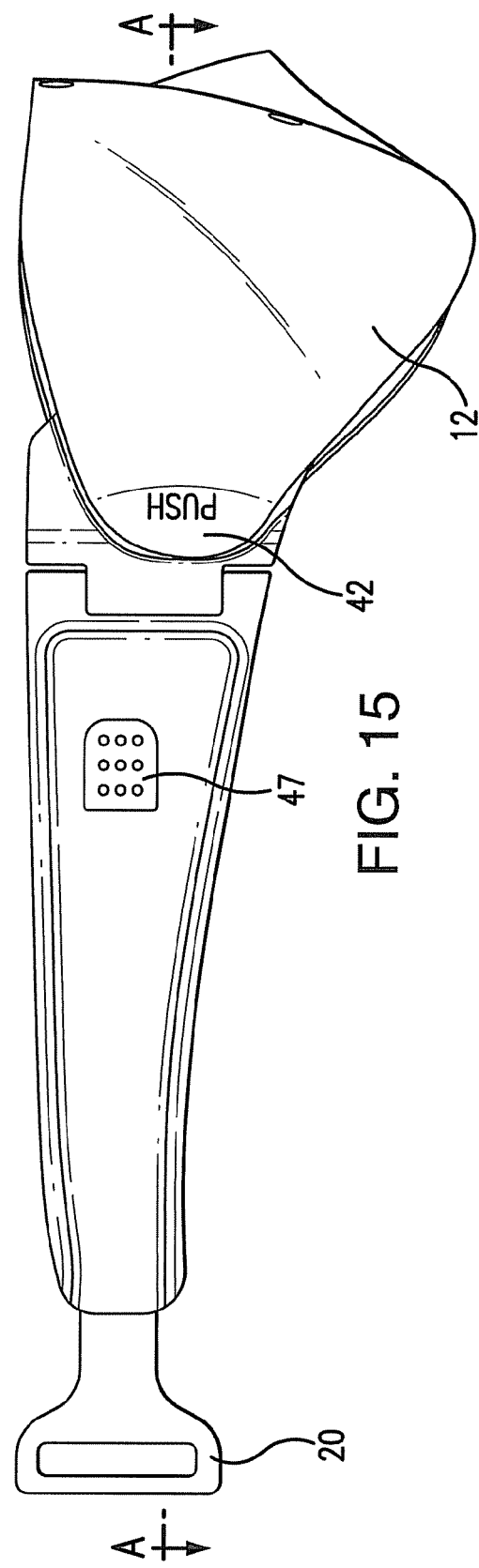
FIG. 15 is a side elevation view of eyewear according to the embodiment illustrated in FIG. 13.

It is preferred that the earstem will be provided with a cover 54 to seal the mechanism within the hollow earstem, as shown in FIG. 13. Further, one or more guides 55 will preferably be provided to guide the movement of components, particularly the lock body 48.

Figure 20:
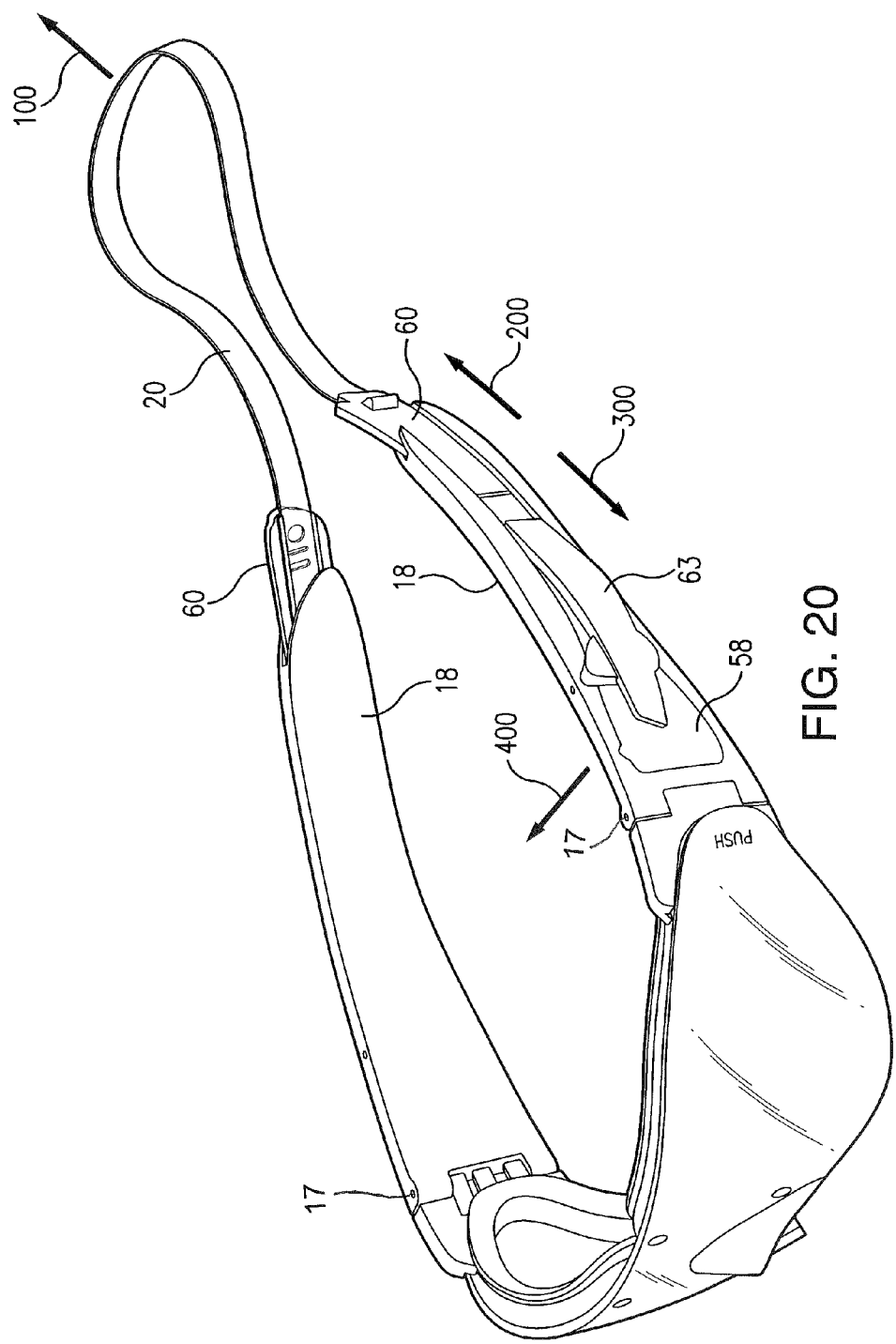
FIG. 20 is an axonometric view of eyewear according to a further embodiment of the present invention showing in alternative mechanism.
Figure 21:
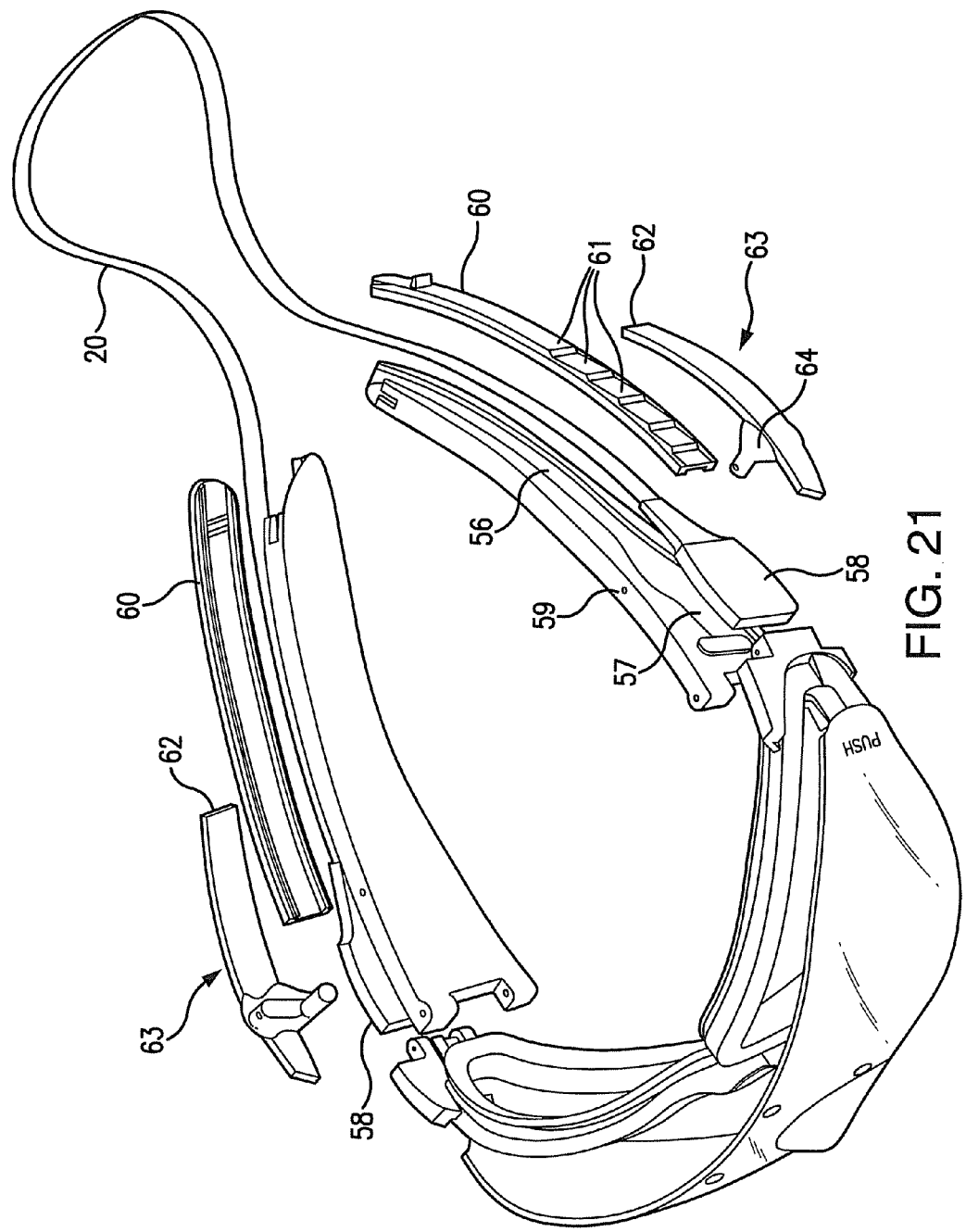
FIG. 21 is an exploded axonometric view of the eyewear illustrated in FIG. 20.
Figure 22:
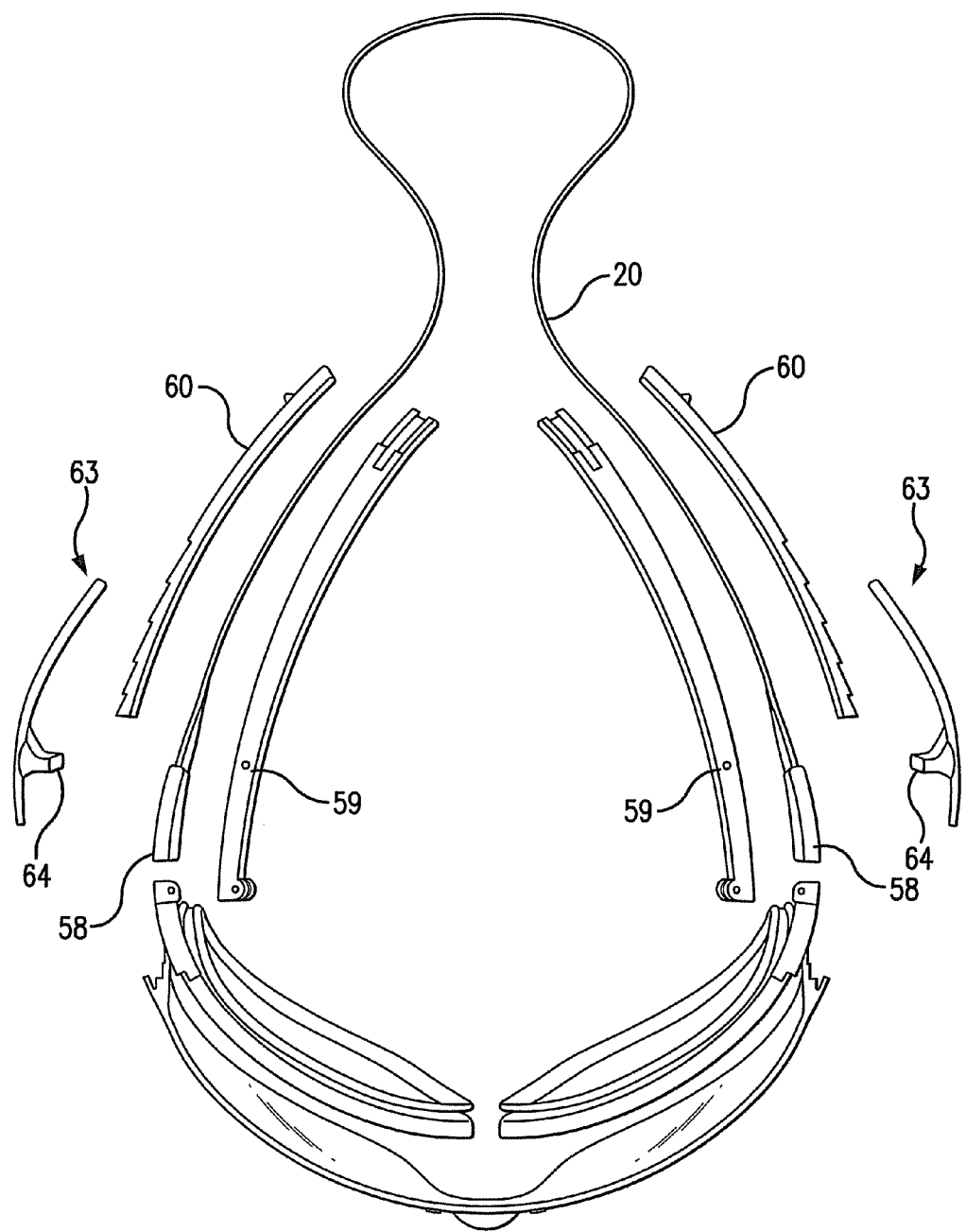
FIG. 22 is an exploded plan view of the eyewear illustrated in FIG. 20.

According to an alternative preferred embodiment illustrated in FIGS. 20 to 22, a configuration can be provided that allows the head strap 20 to form a portion of the tensioning mechanism.

According to this embodiment, the earstems 18 provided are arcuate to match the contours of the side of the wearer's head. Each earstem 18 is provided with an outwardly facing channel 56 therein shaped in use to receive a portion of the head strap 20.

As illustrated in FIG. 21 in particular, the channel 56 is elongate and extends rearwardly to the end of the earstem 18 being shaped to receive the head strap 20 closely within the channel 56 so as to confine a portion of the head strap 20 allowing elongation in a rearward direction only.

A forward portion of the channel 56 on each ear stem 18 is provided with an enlarged opening 57 in order to at least partially receive an enlarged head 58 of the headstrap 20. The enlarged opening 57 constrains the enlarged head 58 of the headstrap 20 to allow elongation of the head strap 20 to create a biasing force.

Normally, each ear stem 18 is provided with a mounting point 59 for pivotally mounting an extender portion 60 relative to each respective earstem 18.

The head strap 20 of this embodiment is typically resilient and has dual functionality being provided as a part of the tensioning mechanism used to drive the frame of the eyewear into the sealed condition and also for normal use as a head strap to hold the eyewear to a person's head. Normally, the eyewear will be worn with the head strap in the extended or primed condition but closely against the user's head in order that a relatively minor shortening of the head strap will drive the eyewear and particularly the frame of the eyewear into the sealed condition against the user's head.

The headstrap 20 of this embodiment is unitary and is attached to the respective ear stem 18 on either side of the eyewear through engagement of the enlarged head portion 58 of the head strap 20 with the enlarged opening 57 provided in the earstem 18. The head strap 20 is elongate and in the preferred form, substantially planar as illustrated.

The head strap 20 is attached to the extender portion 60 which is movable relative to the earstem 18. Normally, the head strap 20 is attached to the extender portion 60 towards the rear of the extender portion 60 which will normally be located adjacent the rear of the ear stem 18.

As illustrated in FIG. 21, the headstrap 20 is located in the channel 56 in the respective ear stem 18 between the ear stem 18 and the extender portion 60.

The extender portion 60 of the illustrated embodiment is arcuate when viewed in plan, corresponding to a least a part of the shape of the ear stem 18 relative to which the extender portion 60 is mounted.

As best illustrated in FIG. 20, the extender portion 60 is received at least partially within an outer portion of the ear stem 18 in order to allow guided movement of the extender portion 60. The movement of the extender portion 60 relative to the ear stem 18 is reciprocal in a forward and rearward direction only.

The extender portion 60 is normally attached to the head strap 20 such that extension of the head strap 20 (movement, usually by hand of the head strap in the direction indicated by arrow 100 in FIG. 20) draws the extender portion 60 rearwardly relative to the ear stem 18 in the direction indicated by arrow 200 in FIG. 20). Any attachment mechanism may be used and normally, the attachment mechanism is provided at a rear of the extender portion 60 in order to attach to the head strap.

A forward outer side of the extender portion 60 is provided with at least part of the latching mechanism in order to temporarily retain the head strap 20 in the extended, elongated or primed condition against the bias of the head strap 20.

One simple mechanism used to latch the extender portion 60 is provision of a number of abutment shoulders 61 against which a catch surface 62 located on the trigger arm 63 abuts. Normally, a number of equally spaced abutment shoulders 62 are provided over a portion of the length of the extender portion 63 as illustrated in FIG. 21, in order to provide an incrementally increasing biasing force.

The configuration of this embodiment also typically includes a trigger arm 63. The trigger arm 63 is provided for the dual purposes of latching against the extender portion 60 in order to hold the head strap 20 in the elongated or primed condition and also to provide a trigger to release the extender portion 60 and the head strap 20 as required to allow the bias of the head strap 20 to move the eyewear and particularly the frame, into the sealed condition against a user's face or head.

According to the illustrated embodiment, the trigger arm 63 is arcuate in shape when viewed in plan having a forward trigger portion and a rearward catch surface 62.

The trigger arm 63 is mounted for pivotal movement relative to the ear stem 18. Preferably, the trigger arm is mounted directly to the ear stem 18 about a pivot point 59. The forward and rearward portions of the trigger arm 63 are typically defined according to the location of the pivot.

Preferably, the pivot on the trigger arm 63 is provided as a pair of spaced apart arms 64 extending substantially transversely from the trigger arm 63 on either side (upper and lower) of the head strap 20 which are mounted to the ear stem 18. Normally, each ear stem 18 is provided with a depression or opening at the pivot point 59 into which a protrusion extending from the spaced apart arms 64 is at least partially received allowing the trigger arm 63 to pivot thereabouts.

The forward portion of the trigger arm 63 overlies and abuts the enlarged head portion 58 of the head strap as illustrated in FIG. 20. Due to the resilience of the head strap 20, the trigger arm 63 is biased by the head portion 58 into the engaged condition about the pivot. Depression of the forward portion of the trigger arm 63 against the enlarged head portion 58 of the head strap (in the direction indicated by arrow 400 in FIG. 20) deforms the enlarged portion 58 of the head strap in order to allow depression of the trigger portion. This releases or disengages the abutment of the catch surface 62 and allows the head strap 20 to shorten (in the direction indicated by arrow 300 in FIG. 20) under the resilient bias in order to draw the eyewear and particularly the frame of the eyewear against the user's head into the sealed condition.

Typically, the trigger arms 63 on both sides of the eyewear are activated at the same time to release the head strap 20 to provide balanced sealing.

Therefore, the head strap of this particular embodiment forms a return spring portion for the trigger arm as well is providing a part of the tension mechanism to draw the eyewear and particularly the frame into the sealed condition against the user's head or face.

In the present specification and claims (if any), the word "comprising" and its derivatives including "comprises" and "comprise" include each of the stated integers but does not exclude the inclusion of one or more further integers.

Reference throughout this specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout this specification are not necessarily all referring to the same embodiment. Furthermore, the particular features, structures, or characteristics may be combined in any suitable manner in one or more combinations.

What is claimed is:

1. Eyewear for use by a wearer, said eyewear providing a substantially fluid tight seal about the wearer's eyes, the eyewear including:
   a. at least one lens for positioning at least partially in front of a wearer's eyes;
   b. a frame adapted to mount the at least one lens for positioning the at least one lens in front of the eyes of the wearer;
   c. a pair of earstems adapted to attach the frame relative to a wearer's head;
   d. at least one seal attached relative to said frame and located about a periphery of the wearer's eyes; and
   e. at least one quick release mechanism including:
      i. an extender portion mounted relative to each of the pair of earstems and including at least one strap;
      ii. a trigger arm attached to each of the pair of earstems and releasably mounted relative to the at least one strap of the respective extender portion;
      iii. a resilient adjustment strap for location about the wearer's head engagable with the at least one extender portion and attached relative to the frame;
   wherein the eyewear is wearable in a substantially fluid tight condition in which the at least one seal forms a substantially fluid tight seal about the wearer's eyes, and a free condition in which the eyewear is wearable with the seal spaced from the wearer's eyes; and
   wherein the eyewear is rapidly adjustable from a primed free mode, in which the trigger arm latches against the respective extender portion to hold the resilient adjustment strap in an extended condition, into a sealed mode, in which the extender portion is released from the respective trigger arm allowing the resilient adjustment strap to force the at least one seal to forms a substantially fluid tight seal about the wearer's eyes.

2. Eyewear as claimed in claim 1, wherein a single unitary or monolithic lens provided extending substantially across the wearer's face.

3. Eyewear as claimed in claim 1 wherein the frame which supports the lenses has a pair of eye rim portions which substantially surround a wearer's eye and are adapted to abut the wearer's face about the eye or eye socket.

4. Eyewear as claimed in claim 3 wherein the at least one seal is a peripheral seal around each of the eye rim portions.

5. Eyewear as claimed in claim 3 wherein the eye rim portions each have an overmoulded seal.

6. Eyewear as claimed in claim 5 wherein the eye rim portions are overmoulded with a resilient material in order to form a seal with the lens at the front of the eyewear.

7. Eyewear as claimed in claim 5 wherein a rear seal is provided peripherally around each of the eye rim portions in order to seal against the user's face when worn in the substantially fluid tight.

8. Eyewear as claimed in claim 7 wherein the rear seal has a resilient extension extending rearwardly from the overmoulded seal including a depending portion in order to abut the user's face.

9. Eyewear as claimed in claim 8 wherein one or more vent openings are provided in the rear seal, these vent openings unobstructed when the eyewear is in the free condition but when the rear seal is deformed during movement to the substantially fluid tight condition, the vent openings are closed.

10. Eyewear as claimed in claim 1 wherein each the earstem is provided with a channel therein to receive a portion of the rear adjustment strap.

11. Eyewear as claimed in claim 10 wherein a forward portion of the channel on each earstem is provided with an enlarged opening in order to at least partially receive an enlarged head of the rear adjustment strap.

12. Eyewear as claimed in claim 10 wherein the rear adjustment strap is attached to the extender portion, which is movable relative to the earstem such that movement of the rear adjustment strap also moves the extender portion relative to the earstem reciprocally in a forward and rearward direction.

13. Eyewear as claimed in claim 12 wherein the extender portion is received at least partially within portion of the earstem in order to allow guided movement of the extender portion.

14. Eyewear as claimed in claim 12 wherein an outer side of the extender portion comprises a number of abutment shoulders in order to temporarily retain the head strap in the extended, elongated or primed condition against the bias of the head strap.

15. Eyewear as claimed in claim 12 further comprising a trigger arm having a forward trigger portion and a rearward catch portion.

16. Eyewear as claimed in claim 15 wherein the rearward catch portion is provided to engage with a portion of the extender portion in order to temporarily retain the head strap in the extended, elongated or primed condition against the bias of the head strap.

17. Eyewear as claimed in claim 16 wherein the trigger arm is mounted for pivotal movement relative to the earstem.

18. Eyewear as claimed in claim 15 wherein a forward portion of the trigger arm overlies an enlarged head of the head strap such that the enlarged head of the head strap provides a resilient return function biasing the forward portion of the trigger arm into an untriggered condition.

19. Eyewear as claimed in claim 1 wherein the frame of the eyewear is flexible to conform to a wearer's face.

* * * * *